US011980499B2

(12) United States Patent
Moriyama et al.

(10) Patent No.: US 11,980,499 B2
(45) Date of Patent: May 14, 2024

(54) MEDICAL DEVICE ASSEMBLY AND RELATED METHODS

(71) Applicant: Boston Scientific Medical Device Limited, Ballybrit (IE)

(72) Inventors: Eduardo Moriyama, Richmond (CA); Kaylie Lau, Toronto (CA); Gareth Davies, Toronto (CA)

(73) Assignee: Boston Scientific Medical Device Limited, Galway (IE)

( * ) Notice: Subject to any disclaimer, the term of this patent is extended or adjusted under 35 U.S.C. 154(b) by 374 days.

(21) Appl. No.: 16/824,776

(22) Filed: Mar. 20, 2020

(65) Prior Publication Data

US 2021/0290200 A1 Sep. 23, 2021

(51) Int. Cl.
| | |
|---|---|
| *A61B 8/00* | (2006.01) |
| *A61B 8/02* | (2006.01) |
| *A61B 8/08* | (2006.01) |
| *A61B 8/12* | (2006.01) |
| *A61B 18/14* | (2006.01) |
| *A61B 18/00* | (2006.01) |

(52) U.S. Cl.
CPC ............... *A61B 8/445* (2013.01); *A61B 8/02* (2013.01); *A61B 8/0883* (2013.01); *A61B 8/12* (2013.01); *A61B 18/1492* (2013.01); *A61B 2018/00351* (2013.01)

(58) Field of Classification Search
None
See application file for complete search history.

(56) References Cited

U.S. PATENT DOCUMENTS

| | | | |
|---|---|---|---|
| 2006/0142660 A1* | 6/2006 | Maschke | A61N 1/056 600/466 |
| 2007/0078500 A1* | 4/2007 | Ryan | A61B 5/0075 607/88 |
| 2008/0146942 A1* | 6/2008 | Dala-Krishna | A61B 8/4461 600/466 |
| 2009/0088648 A1* | 4/2009 | Jaffe | A61B 5/0084 600/466 |
| 2010/0280316 A1* | 11/2010 | Dietz | A61B 17/3478 600/101 |

* cited by examiner

*Primary Examiner* — Joel Lamprecht
(74) *Attorney, Agent, or Firm* — Nelson Mullins Riley & Scarborough LLP

(57) ABSTRACT

A method for carrying out a cardiac procedure includes a. engaging a shaft of an ultrasound catheter with an elongate member of a medical sheath; b. positioning an ultrasound tip of the ultrasound catheter outside of a lumen of the elongate member; c. intravenously advancing the elongate member of the medical sheath towards a heart of a patient, to position a distal end of the elongate member adjacent a target anatomy within the heart; d. using the medical sheath as a guide to intravenously advance the ultrasound catheter towards the heart of the patient and position the ultrasound tip proximate the target anatomy; and e. using the ultrasound tip to image the target anatomy.

14 Claims, 10 Drawing Sheets

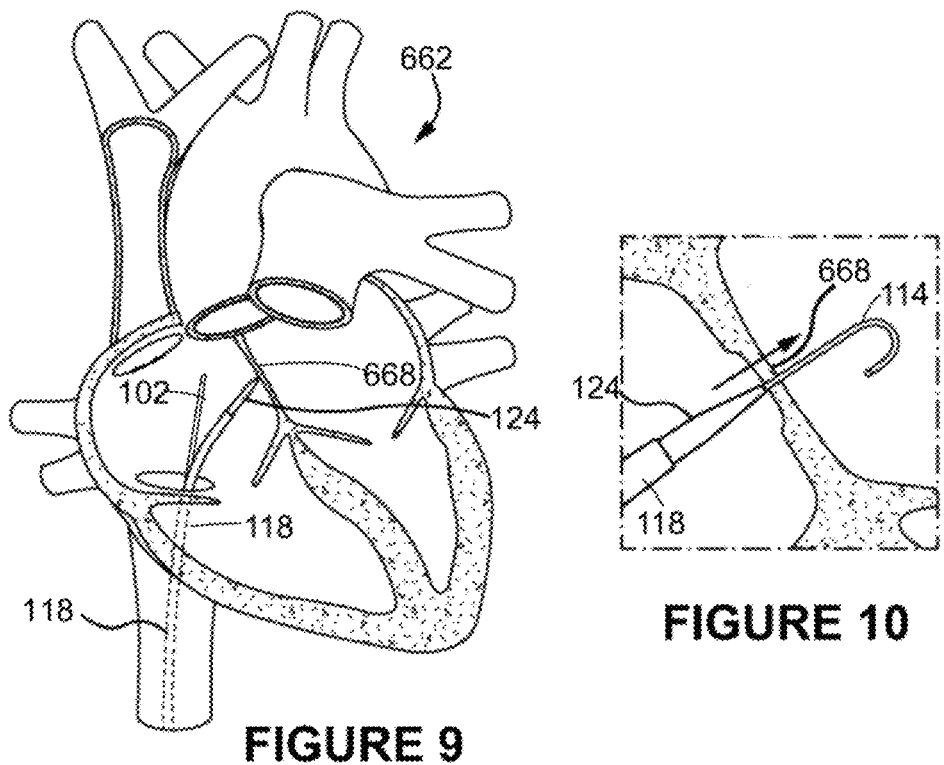
FIGURE 9
FIGURE 10
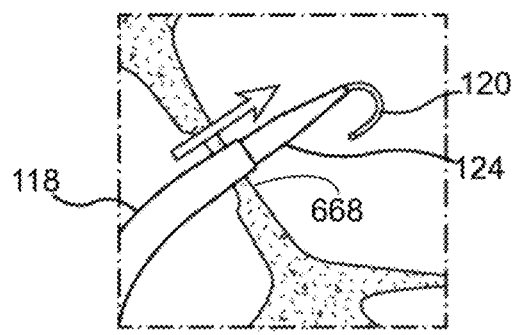
FIGURE 11

MEDICAL DEVICE ASSEMBLY AND RELATED METHODS

FIELD

This document relates to cardiac procedures that use ultrasound imaging. More specifically, this document relates to assemblies of medical devices, which are usable in cardiac procedures involving ultrasound imaging, and related methods.

SUMMARY

The following summary is intended to introduce the reader to various aspects of the detailed description, but not to define or delimit any invention.

Methods for carrying out cardiac procedures are disclosed. According to some aspects, a method for carrying out a cardiac procedure includes a. engaging a shaft of an ultrasound catheter with an elongate member of a medical sheath; b. positioning an ultrasound tip of the ultrasound catheter outside of a lumen of the elongate member; c. intravenously advancing the elongate member of the medical sheath towards a heart of a patient, to position a distal end of the elongate member adjacent a target anatomy within the heart; d. using the medical sheath as a guide to intravenously advance the ultrasound catheter towards the heart of the patient and position the ultrasound tip proximate the target anatomy; and e. using the ultrasound tip to image the target anatomy.

In some examples, step a. includes advancing the ultrasound catheter along a longitudinal axis of the elongate member, and step b. includes advancing the ultrasound catheter along a longitudinal axis of the elongate member.

In some examples, steps a. and b. are carried out before steps c. and d., and steps c. and d. are carried out concurrently.

In some examples, step a. includes inserting the ultrasound catheter into the lumen of the elongate member.

In some examples, step b. includes passing the ultrasound tip through an aperture in the elongate member.

In some examples, step a. includes securing the shaft of the ultrasound catheter to an exterior surface of the elongate member.

In some examples, step a. includes engaging the shaft of the ultrasound catheter with a catch of the elongate member.

In some examples, step c. includes curving the medical sheath to steer the distal end towards the target anatomy.

Medical devices assemblies are also disclosed. According to some aspects, a medical device assembly includes an ultrasound catheter and a medical sheath. The ultrasound catheter includes an elongate shaft having a shaft proximal portion, an opposed shaft distal portion, and a shaft central portion between the shaft proximal portion and the shaft distal portion. An ultrasound tip is at the shaft distal portion. The medical sheath includes an elongate member having an elongate member proximal portion defining an elongate member proximal end, an opposed elongate member distal portion defining an elongate member distal end, and an elongate member central portion between the elongate member proximal portion and the elongate member distal portion. The elongate member central portion defines a longitudinal axis of the elongate member, and the elongate member distal portion includes a curved section that spaces the elongate member distal end away from the longitudinal axis. The medical sheath further includes a lumen extending through the elongate member from the elongate member proximal portion to the elongate member distal portion, and a catch for engaging the shaft of the ultrasound catheter. The shaft is engaged with the catch, the shaft central portion extends along the elongate member central portion, and the shaft distal portion and the ultrasound tip are positioned outside of the lumen of the elongate member and are spaced longitudinally from the elongate member distal end.

In some examples, the shaft central portion is received in the lumen.

In some examples the catch includes an aperture in the curved section, and the shaft passes through the aperture to position the shaft distal portion and ultrasound tip outside of the lumen.

In some examples, the elongate member includes a second lumen for receiving an additional medical device.

In some examples, the entirety of the shaft is outside of the lumen.

In some examples, the catch includes a longitudinally extending groove on an exterior surface of the elongate member, and the shaft central portion is received in the groove.

In some examples, the catch includes a clip on an exterior surface of the elongate member, and the shaft central portion is received in the clip.

In some examples, the elongate member is steerable to impart the curved section to the elongate member distal portion.

BRIEF DESCRIPTION OF THE DRAWINGS

The accompanying drawings are for illustrating examples of articles, methods, and apparatuses of the present disclosure and are not intended to be limiting. In the drawings:

FIG. 9 is a schematic view showing a fourth step of the method of FIG. 6;

FIG. 10 is a schematic view showing a fifth step of the method of FIG. 6;

FIG. 11 is a schematic view showing a sixth step of the method of FIG. 6.

DETAILED DESCRIPTION

Figure 1:
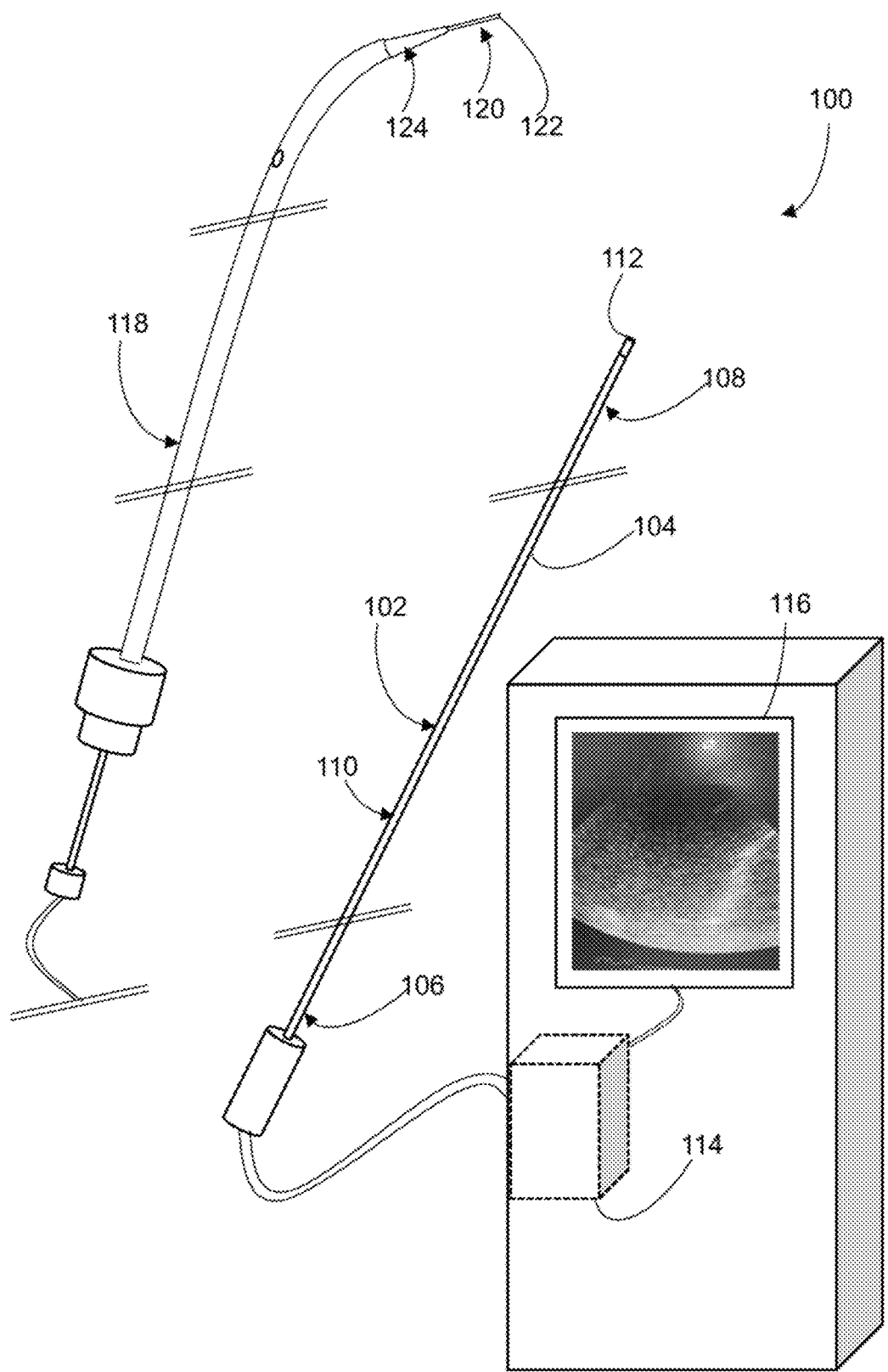
FIG. 1 is a perspective view of an example medical system.

Various apparatuses or processes or compositions will be described below to provide an example of an embodiment of the claimed subject matter. No example described below limits any claim and any claim may cover processes or apparatuses or compositions that differ from those described below. The claims are not limited to apparatuses or processes or compositions having all of the features of any one apparatus or process or composition described below or to features common to multiple or all of the apparatuses or processes or compositions described below. It is possible that an apparatus or process or composition described below is not an embodiment of any exclusive right granted by issuance of this patent application. Any subject matter described below and for which an exclusive right is not granted by issuance of this patent application may be the subject matter of another protective instrument, for example, a continuing patent application, and the applicants, inventors or owners do not intend to abandon, disclaim or dedicate to the public any such subject matter by its disclosure in this document.

Generally disclosed herein is an assembly of medical devices that can be used in medical procedures, such as cardiac procedures. The assembly can include a medical sheath (also referred to herein simply as a "sheath") and an ultrasound catheter (also referred to herein as a "U/S catheter"), which are engageable together to allow for the sheath to guide the U/S catheter to a target site within the body. For example, the assembly can be used in transseptal perforation procedures, in which the sheath is advanced to the right atrium of a patient's heart via the femoral vein. The sheath can act as a guide for U/S catheter, which can also be advanced to the right atrium of a patient's heart via the femoral vein. The U/S catheter can be engaged with the sheath and advanced to the right atrium concurrently with the sheath, or engaged with the sheath and advanced to the right atrium after the sheath is advanced. The U/S catheter can be advanced through a lumen of the sheath, or can be positioned on the exterior of the sheath. Once in position in the right atrium, the US catheter can be used to image the heart and/or other parts of the system, for example to gain information about the heart and/or to confirm positioning of the sheath. A perforation device (e.g. a radiofrequency (RF) perforation device or a mechanical perforation device) and dilator can also be guided through the sheath to the right atrium, either concurrently with the sheath or after the sheath has been advanced. With the sheath adjacent the target location in the right atrium, for example the fossa ovalis of the atrial septum, the perforation device can be advanced out of the sheath and used to create a perforation in the target location, and the dilator can be advanced out of the sheath to dilate the perforation. During perforation and dilation, the US catheter can be used to image the heart and/or other parts of the system, e.g. to confirm the positioning of the perforation device. Such procedures can be carried out, for example, as a medical treatment, or to gain access to the left atrium for a subsequent medical treatment.

By engaging the U/S catheter with the sheath and advancing the U/S catheter via the same access point as the sheath, the number of access points in the body can be reduced, which can enhance patient safety. Furthermore, by positioning the U/S catheter directly in the heart, the visualization of the atrial septum and the perforation device can be improved. Furthermore, by engaging the U/S catheter with the sheath, the number of device exchanges can be reduced, which can streamline the surgical workflow.

The U/S catheters disclosed herein can optionally be 3-dimensional ultrasound catheters (e.g. an intracardiac echocardiography (ICE) catheter).

Referring now to FIG. 1, an example medical system 100 (also referred to herein simply as a 'system') is shown. In the example shown, the system 100 includes a U/S catheter 102, for emitting ultrasound signals to an anatomical volume and receiving reflected ultrasound signals from the anatomical volume. The U/S catheter 102 can be, for example, an ICE catheter. The U/S catheter 102 generally includes an elongate shaft 104, which has a proximal portion 106 (also referred to herein as a 'shaft proximal portion'), a distal portion 108 (also referred to herein as a 'shaft distal portion'), and a central portion 110 (also referred to herein as a 'shaft central portion') between the proximal portion 106 and the distal portion 108. An ultrasound tip 112, which emits ultrasound signals to the anatomical volume and receives reflected ultrasound signals from the anatomical volume, is at the shaft distal portion 108. Various additional electronic components (not shown) are within or mounted to the shaft 104, to connect the ultrasound tip 112 to an ultrasound data processor 114 (described below) of the system 100.

Referring still to FIG. 1, the ultrasound data processor 114 is connected or connectable to the U/S catheter 102. Ultrasound data based on the reflected ultrasound signals is sent from the U/S catheter 102 to the ultrasound data processor 114 (via hardware within the shaft 104, not shown), and the ultrasound data processor 114 receives and processes the ultrasound data using, for example, standard software features. The system 100 further includes an imaging system 116 connected to the ultrasound data processor 114 for generating an image (e.g. a 3-dimensional visual model) of the anatomical volume, based on the processed data.

Such U/S catheters 102, ultrasound data processors 114, and U/S imaging systems 116 are known in the art, are often sold together as an all-in-one system (e.g. such systems are sold by Siemens Healthcare GmbH or by General Electric Company), and will not be described in detail herein.

Referring still to FIG. 1, the system 100 further includes a sheath 118. As will be described in further detail below, the sheath 118 can engage the U/S catheter 102, and can guide the U/S catheter 102 to a target location within a patient's body, e.g. to the right atrium of the heart. Furthermore, the sheath 118 can receive various medical devices (including the U/S catheter 102, as will be described below), which can be advanced to the target location within a patient's anatomy.

The system 100 can further include one or more treatment devices. Referring still to FIG. 1, in the example shown, the system 100 includes a radiofrequency perforation device 120 having a perforating tip 122, and a dilator 124, which can both be advanced towards the target location in the patient's heart via the sheath 118 (in FIG. 1, the radiofrequency perforation device is within the dilator, and the dilator is within the sheath, and only the distal ends of each are visible). The radiofrequency perforation device 120 can be connected to a radiofrequency generator (not shown), which can in turn be connected to one or more grounding pads (not shown). Radiofrequency perforation devices, generators, and grounding pads, as well as dilators, are known in the art, and will not be described in detail herein. Examples are sold by Baylis Medical Company, Inc. (Montreal, Canada), for example under the brand names NRG® Transseptal Platform, or SupraCross® Transseptal Platform.

In alternative examples, alternative or additional treatment devices may be part of the system.

Figure 2:
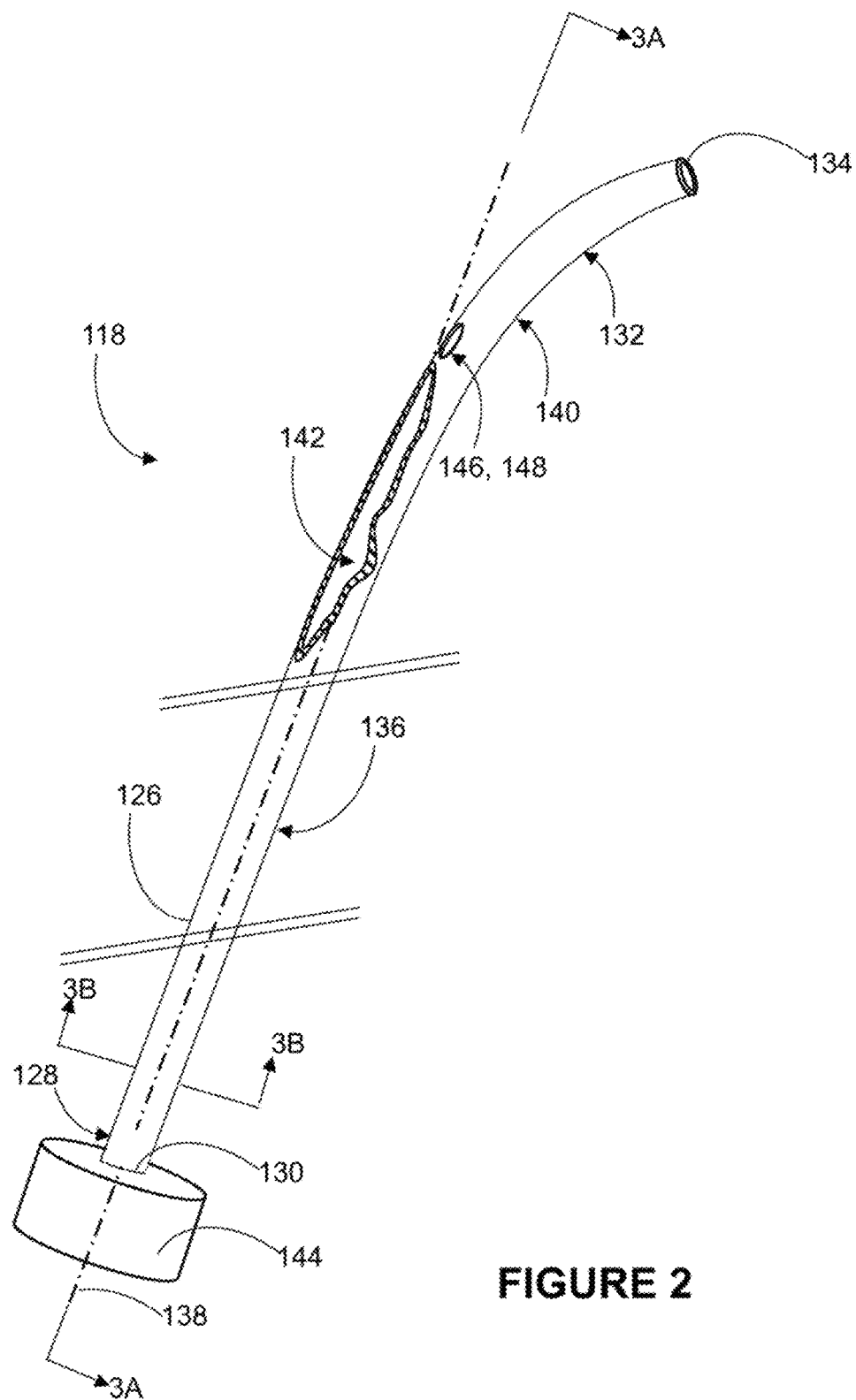
FIG. 2 is a perspective cutaway view of the sheath of the system of FIG. 1.

Referring now to FIG. 2, the sheath 118 is shown in greater detail. In the example shown, the sheath 118 includes an elongate member 126. The elongate member 126 has a proximal portion 128 (also referred to herein as an 'elongate member proximal portion') that defines a proximal end 130 of the elongate member 126 (also referred to herein as an 'elongate member proximal end'), a distal portion 132 ('also referred to herein as an 'elongate member distal portion') opposite the proximal portion 128, which defines a distal end 134 (also referred to herein as an 'elongate member distal end') of the elongate member 126, and a central portion 136 (also referred to herein as an 'elongate member central portion') between the proximal portion 128 and the distal portion 132. The central portion 136 is generally linear and defines a longitudinal axis 138 of the elongate member 126. The distal portion 132 includes a curved section 140 that spaces the distal end 134 away from the longitudinal axis 138. The curved section 140 can optionally be a fixed curved section, or the elongate member 126 can be 'steerable' to selectively impart the curved section to the elongate member 126. A lumen 142 extends through the elongate member 126, from the proximal portion 128 to the distal portion 132. The lumen 142 is open at the distal end 134 of the elongate member 126 The lumen 142 can receive various medical devices (including the U/S catheter, as will be described below), which can be advanced to a target location within a patient's anatomy via the lumen 142.

Referring still to FIG. 2, in the example shown, a handle 144 is mounted to the proximal portion 128 of the elongate member 126. The handle 144 can include various hubs and/or ports and/or connection points (not shown) for connection to various external devices.

Figure 3A:
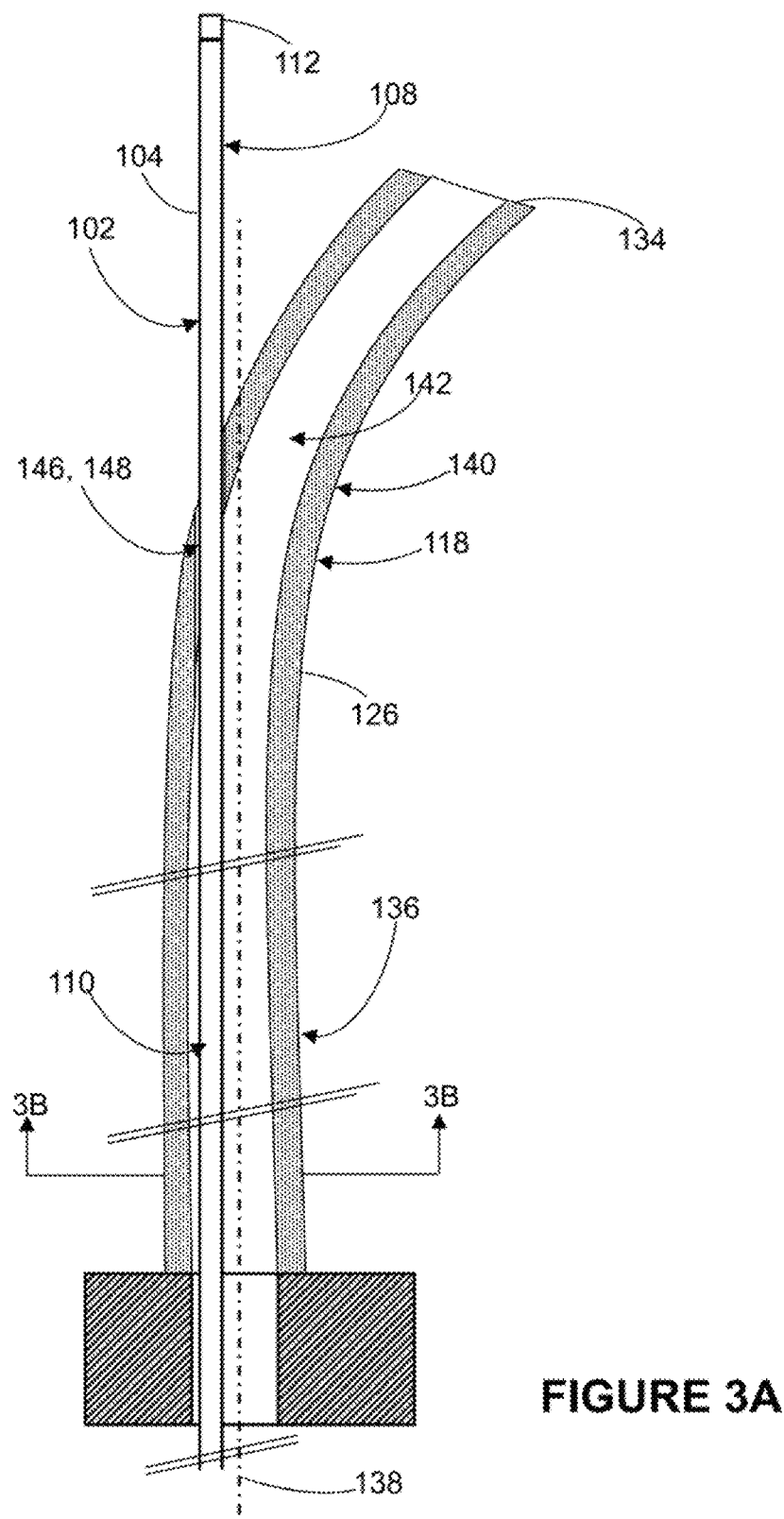
FIG. 3A is a cross-section taken along line 3A-3A in FIG. 2, also showing an ultrasound catheter engaged with the sheath.

Referring to FIG. 3A, the sheath 118 is configured to engage the U/S catheter 102 so that in use, the sheath 118 can be used as a guide for the U/S catheter 102 (e.g. as a guide to intravenously advance the U/S catheter 102 towards the heart of the patient). In order to engage the U/S catheter 102, the sheath includes a catch 146, described in further detail below, for engaging the shaft 104 of the ultrasound catheter 102. When the sheath 118 and the U/S catheter 102 are engaged and in the in use position (shown in FIG. 3A), the shaft central portion 110 extends longitudinally along the elongate member central portion 136 (either inside of the lumen 142 as in the example of FIG. 3A, or outside of the lumen as in the example of FIGS. 4A to 5B), and the shaft distal portion 108 and the ultrasound tip 112 are positioned outside of the lumen 142 of the elongate member 126 and spaced longitudinally from the elongate member distal end 134. When the sheath 118 and the U/S catheter 102 are engaged and in the in use position, and the sheath 118 is positioned with the distal end 134 thereof at or proximate a target location within a patient's anatomy (e.g. within the left atrium of the heart), the ultrasound tip 112 is positioned to image the target location.

As mentioned above, the sheath 118 includes a catch 146 for engaging the shaft 104 of the U/S catheter 102. The catch 146 can be of various configurations.

In the example of FIG. 3A, the catch 146 is in the form of an aperture 148 in the curved section 140 of the elongate member 126. In this example, when the sheath 118 and the U/S catheter 102 are engaged and in the in use position, the shaft central portion 110 is received in the lumen 142, and the shaft 104 passes through the aperture 148 to position the shaft distal portion 108 and ultrasound tip 112 outside of the lumen 142.

Figure 3B:
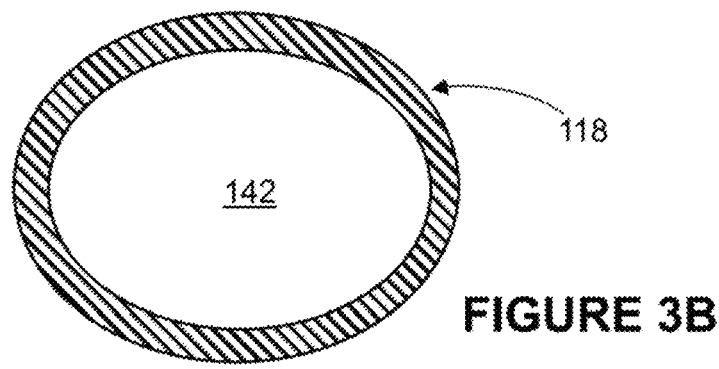
FIG. 3B is a cross-section taken along line 3B-3B in FIG. 2.
Figure 3C:
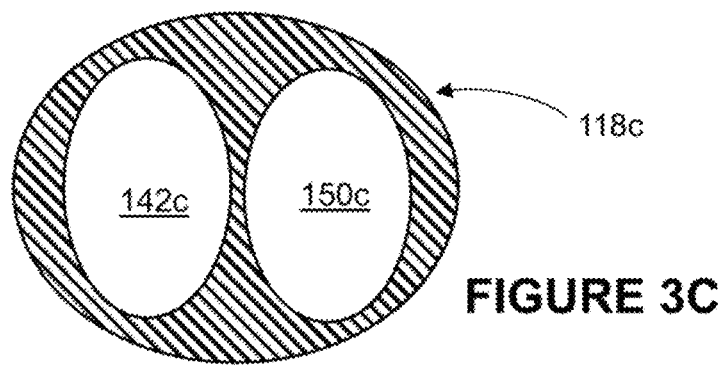
FIG. 3C is a cross-section similar to that of FIG. 3B, taken through another example sheath.
Figure 3D:
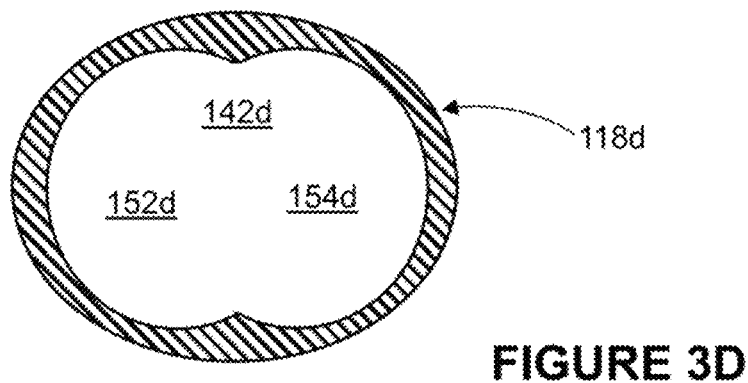
FIG. 3D is a cross-section similar to that of FIG. 3B, taken through another example sheath.

In the example of FIG. 3A, the sheath 118 includes a single lumen 142, shown also in FIG. 3B, for receiving the shaft 104 as well as for receiving additional medical devices (e.g. the radiofrequency perforation device 120 and dilator 124). In alternative examples, as shown in FIG. 3C (wherein features are referred to with like reference numerals as in FIGS. 1 to 3A, with the suffix 'c'), the sheath 118c can include an additional lumen 150c (also referred to as a 'second lumen'), which is separate from the lumen 142c, for receiving additional medical devices. In further alternative examples, as shown in FIG. 3D (wherein features are referred to with like reference numerals as in FIGS. 1 to 3A, with the suffix cd'), the sheath 118d includes a lumen 142d that is be divided, to create a first section 152d for receiving the U/S catheter 102 and a second section 154d for receiving additional medical devices.

Figures 4A, 4B:
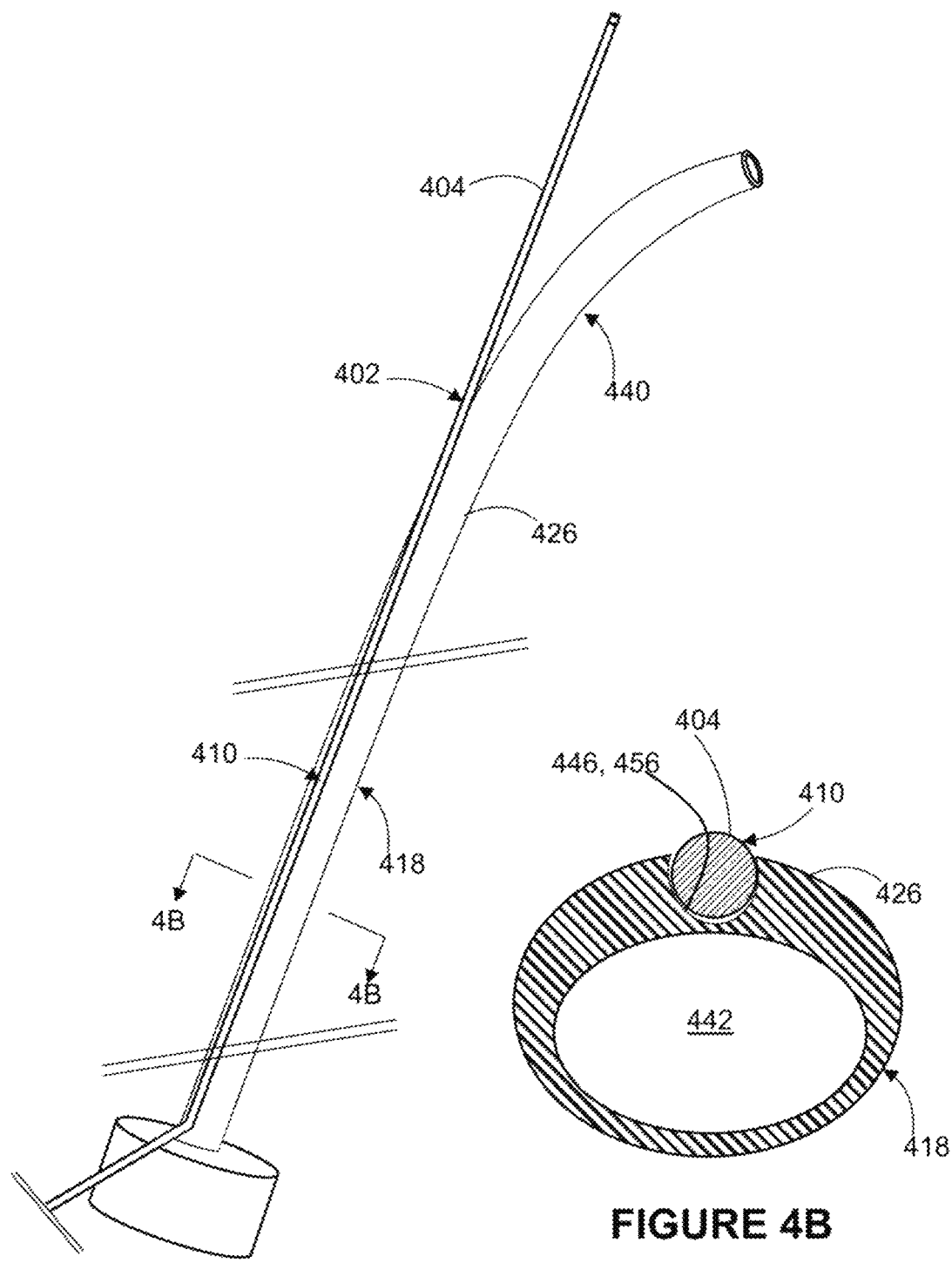
FIG. 4A is a perspective view of another example sheath with an ultrasound catheter engaged with the sheath.
FIG. 4B is a cross-section taken along line 4B-4B in FIG. 4A.

Referring to FIGS. 4A and 4B (in which features are referred to with like reference numerals as in FIGS. 1 to 3A, incremented by 300) another example assembly is shown, which include an alternative example sheath 418. In the example of FIGS. 4A and 4B, the entirety of the shaft 404 of the U/S catheter 402 is outside the lumen 442. The catch 446 is in the form of a longitudinally extending groove 456 (shown in FIG. 4B) on an exterior surface of the elongate member 426, which extends along the elongate member 426 to the curved section 440 of the elongate member. The shaft central portion 410 is received in the groove 456, to secure the U/S catheter 102 to the elongate member 426.

Figures 5A, 5B:
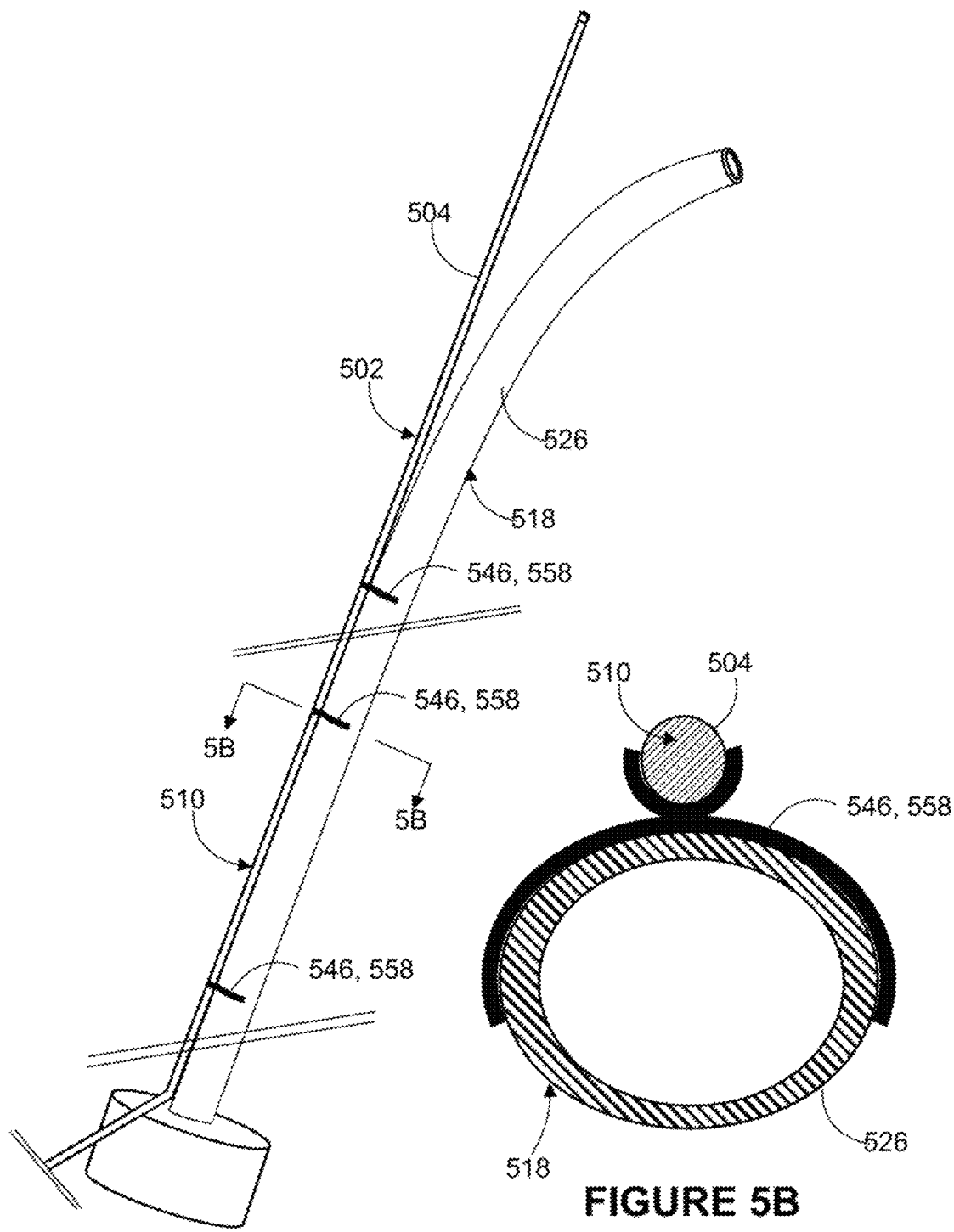
FIG. 5A is a perspective view of another example sheath with an ultrasound catheter engaged with the sheath.
FIG. 5B is a cross-section taken along line 5B-5B in FIG. 4A.

Referring to FIGS. 5A and 5B (in which features are referred to with like reference numerals as in FIGS. 1 to 3A, incremented by 400), another example assembly is shown. In this example, the catch 546 is in the form of a clip 558 on an exterior surface of the elongate member 526. Optionally, more than one clip 558 can be provided, as shown. The clip(s) 558 can receive the central portion 510 of the shaft 504, to secure the U/S catheter 502 to the elongate member 526 of the sheath 518.

Referring now to FIGS. 6 to 11, a method for carrying out a cardiac procedure, specifically for creation of a transseptal perforation, will be described. The method will be described with reference to the assembly shown in FIG. 3A; however, variations of the method can be carried out with alternative assemblies, such as those shown in FIGS. 4A to 5B.

Figure 6:
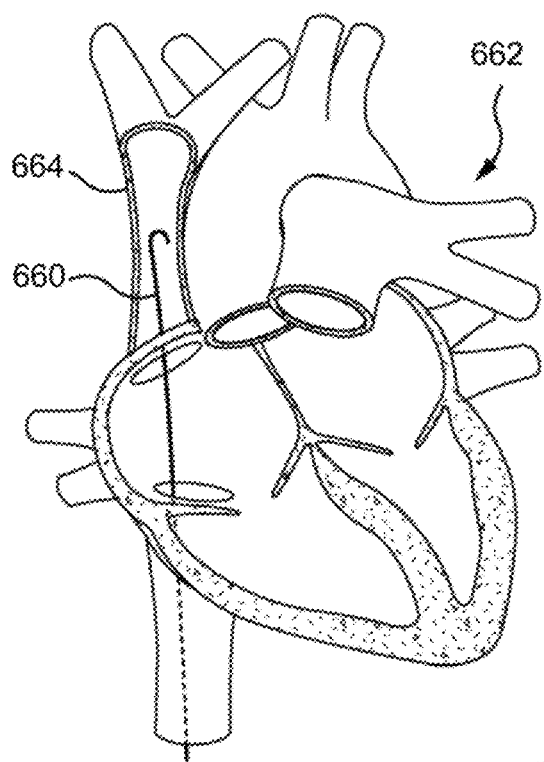
FIG. 6 is a schematic view showing a first step of an example method for carrying out a cardiac procedure.

Referring to FIG. 6, a guidewire 660 can be advanced via the femoral vein towards the heart 662, and "parked" in the superior vena cava (SVC) 664.

Figure 7:
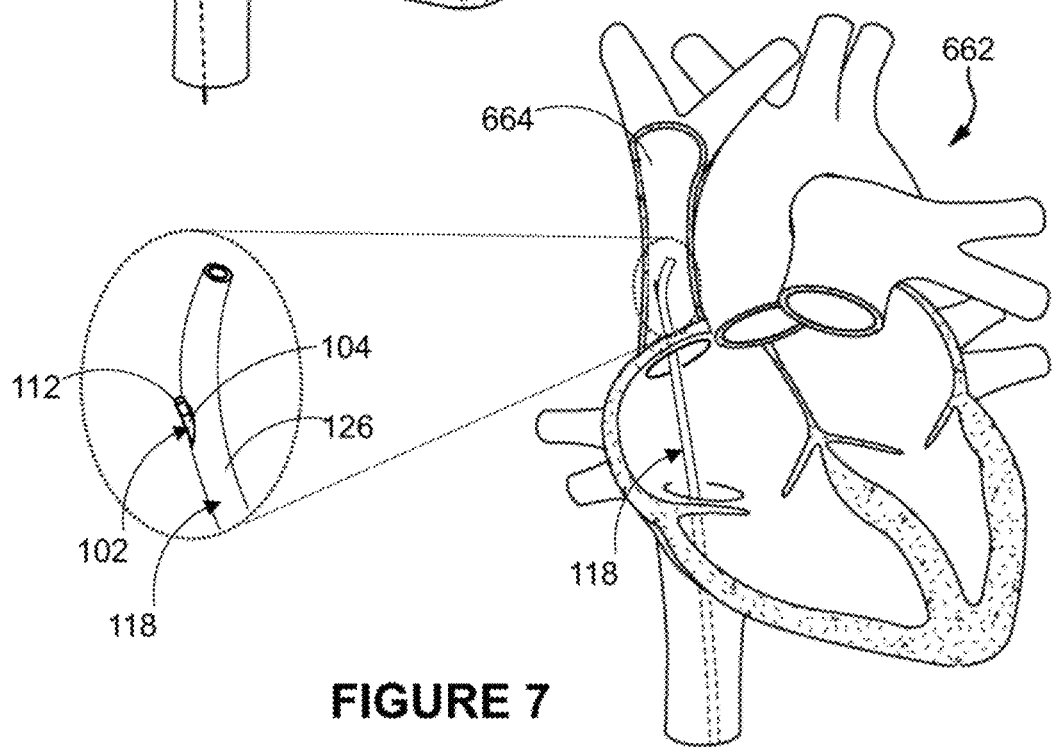
FIG. 7 is a schematic view showing a second step of the method of FIG. 6.

The U/S catheter 102 can then be engaged with the sheath 118, and the sheath 118 can then intravenously guide the U/S catheter 102 towards the SVC 664. Specifically, the assembly can be prepared by inserting the U/S catheter 102 into the lumen 142) of the elongate member 126 and advancing the U/S catheter in the longitudinal direction until the ultrasound tip 112 passes through the aperture 148 and is outside the lumen 142, just proud of the aperture 148. The dilator 124 can also be inserted into the sheath 118, with the tip of the dilator 124 shrouded within the sheath 118. Referring to FIG. 7, the sheath 118 and dilator 124 (not visible in FIG. 7) can then be advanced over the guidewire 660 (not visible in FIG. 7), towards the SVC 664. During advancement, the sheath 118 serves as a guide for the U/S catheter 102, so that the U/S catheter 102 is also intravenously advanced towards the SVC 664. The guidewire 660 can then be removed, so that the assembly is in the position shown in FIG. 7, with the ultrasound tip 112 outside the lumen 142, just proud of the aperture 148.

The RF perforation device 120 (not visible in FIG. 7) can then be advanced through the dilator 124 until the perforating tip 122 (not visible in FIG. 7) of the RF perforation device 120 is just shy of the distal end of the dilator 124.

Figure 8:
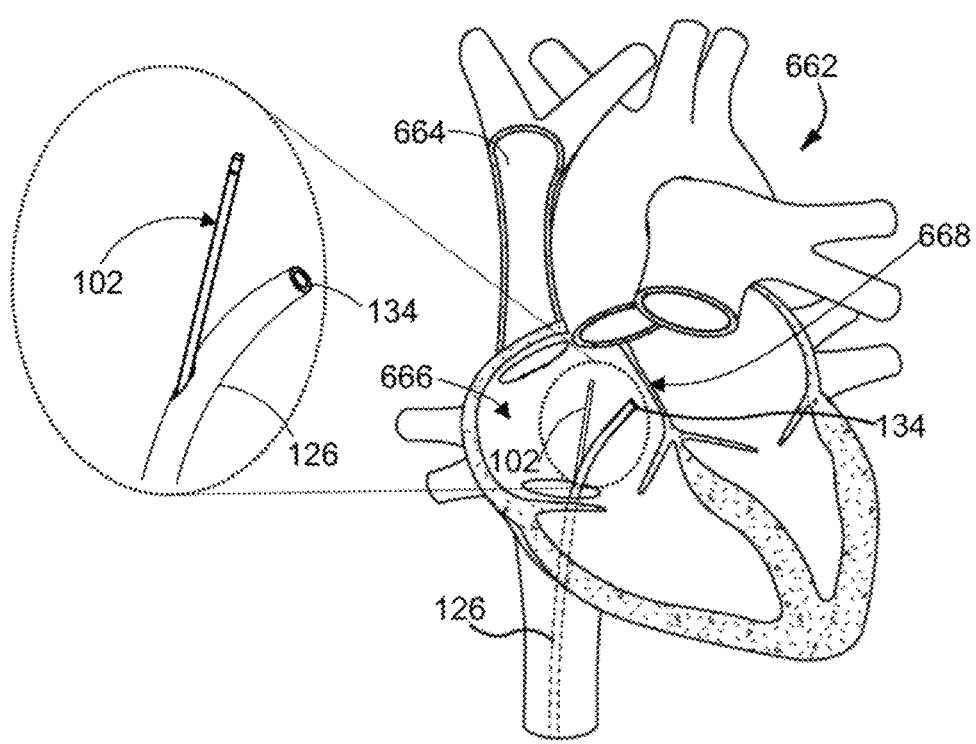
FIG. 8 is a schematic view showing a third step of the method of FIG. 6.

With the ultrasound tip 112 still just proud of the aperture 148 and with the dilator 124 and radiofrequency perforation device 120 shrouded in the sheath 118, the distal end 134 of the elongate member 126 can then be advanced towards a target location in the patient's heart 662, e.g. to the right atrium 666 of the patient's heart 662, to position the distal end 134 of the elongate member 126 adjacent the target location. The target location can be for example, the fossa ovalis 668 of the atrial septum. Referring to FIG. 8, with the distal end 134 of the elongate member 126 in position in the right atrium 666, the U/S catheter 102 can then be advanced slightly in the longitudinal direction, to the in use position, so that the target location can be imaged. The U/S catheter 102, ultrasound data processor 104, and imaging system 106 (not shown in FIG. 8) can then be used to image the heart 662 and/or the various parts of the system. For example, the fossa ovalis 668 and/or the perforating tip 122 can viewed on the ultrasound image.

Figure 12:
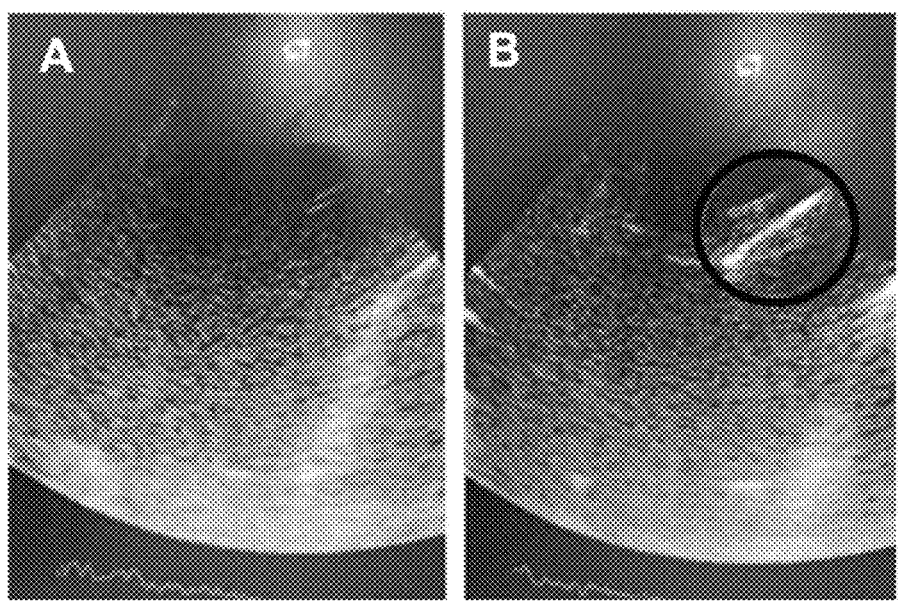
FIG. 12 is an example of an ultrasound image that can be captured using the method of FIGS. 6 to 11.

Referring to FIGS. 9 to 11, the perforation device 120 can then be engaged to perforate the fossa ovalis 668, and the dilator 124 can be advanced from the sheath 118 to dilate the perforation. The sheath 118 can then be advanced through the perforation, to the left atrium. During perforation and dilation, the U/S catheter 102, ultrasound data processor 104, and imaging system 106 (not shown in FIG. 7) can be used to image the heart and/or various parts of the system. An example of such an image is shown in FIG. 12, wherein panel A shows an example ultrasound image generated using this method, prior to advancing the perforation device 120 to perforate the fossa ovalis, and panel B shows an example ultrasound image generated using this method, after advancing the perforation device 120 (circled) to perforate the fossa ovalis.

Once access to the left atrium has been gained, a subsequent medical treatment (not shown) can be carried out.

Upon completion of the medical treatment or at a desired time, the dilator 124, perforation device 120, sheath 118 and U/S catheter 102 can be withdrawn from the heart 402.

The engagement of the U/S catheter 102 with the sheath 118 can be done at various points in the method. In the method described above, the U/S catheter 102 is engaged with the sheath 118 prior to advancing the sheath 118 into the patient's body, and the U/S catheter 102 is advanced into the patient's body concurrently with the sheath 118. In alternative examples, the U/S catheter 102 can be engaged with the sheath 118 and advanced along the sheath 118 after the sheath 118 has been inserted into the patient's body.

In alternative methods, the devices of FIG. 4 or 5 can be used. Such methods are similar to the method described above; however, in such methods, rather than advancing the U/S catheter 102 into the lumen 142, the U/S catheter 102 can be secured to the exterior surface of the elongate member 426 or 526—i.e. by sliding the shaft 104 into the groove 456 of the elongate member 426 or into the clips 558 of the elongate member 526.

While the above description provides examples of one or more processes or apparatuses or compositions, it will be appreciated that other processes or apparatuses or compositions may be within the scope of the accompanying claims.

To the extent any amendments, characterizations, or other assertions previously made (in this or in any related patent applications or patents, including any parent, sibling, or child) with respect to any art, prior or otherwise, could be construed as a disclaimer of any subject matter supported by the present disclosure of this application, Applicant hereby rescinds and retracts such disclaimer. Applicant also respectfully submits that any prior art previously considered in any related patent applications or patents, including any parent, sibling, or child, may need to be re-visited.

We claim:

1. A method for carrying out a cardiac procedure, comprising the steps of:
    a. engaging an ultrasound catheter having an ultrasound tip with a medical sheath, the ultrasound tip being configured to emit ultrasound signals and receive reflected ultrasound signals and the medical sheath having a curved section including an aperture, wherein engaging the ultrasound catheter with the medical sheath includes advancing the ultrasound catheter along a longitudinal lumen of the medical sheath until the ultrasound tip engages the aperture;
    b. intravenously advancing the medical sheath towards a heart of a patient, and then positioning a distal end of the medical sheath adjacent a target anatomy within the heart;
    c. intravenously advancing the ultrasound catheter along the longitudinal axis, through the aperture, and past a distal end of the medical sheath to position the ultrasound tip proximate the target anatomy; and
    d. using the ultrasound tip to image the target anatomy.

2. The method of claim 1, wherein step a is carried out before steps b and c.

3. The method of claim 1, wherein step a. comprises securing a shaft of the ultrasound catheter to an exterior surface of the medical sheath.

4. The method of claim 1, wherein step a. comprises engaging a shaft of the ultrasound catheter with a catch of the medical sheath.

5. The method of claim 1, further comprising advancing a dilator and perforation device through the lumen of the medical sheath.

6. The method of claim 1, wherein step b. comprises steering the distal end towards the target anatomy.

7. A medical device assembly comprising:
    an ultrasound catheter including (i) an elongate shaft having a shaft proximal portion, an opposed shaft distal portion, and a shaft central portion between the shaft proximal portion and the shaft distal portion, and (ii) an ultrasound tip at the shaft distal portion, the ultrasound tip being configured to emit ultrasound signals and receive reflected ultrasound signals; and
    a medical sheath including (i) an elongate member having an elongate member proximal portion defining an elongate member proximal end, an opposed elongate member distal portion defining an elongate member distal end, and an elongate member central portion between the elongate member proximal portion and the elongate member distal portion, wherein the elongate member central portion defines a longitudinal axis of the elongate member, and the elongate member distal portion includes a curved section that spaces the elongate member distal end away from the longitudinal axis; (ii) a lumen extending through the elongate member from the elongate member proximal portion to the elongate member distal portion; and (iii) an aperture in the curved section aligned with the longitudinal axis of the elongate member;

wherein the shaft distal portion and the ultrasound tip pass through the aperture and are positioned outside of the lumen of the elongate member along the longitudinal axis of the elongate member, such that the ultrasound tip is spaced longitudinally from the elongate member distal end.

8. The medical device assembly of claim 7, wherein the shaft central portion is received in the lumen.

9. The medical device assembly of claim 7, wherein the elongate member is steerable to impart the curved section to the elongate member distal portion.

10. The medical device assembly of claim 7, wherein the elongate member comprises a second lumen for receiving an additional medical device.

11. A medical device assembly comprising:
an ultrasound catheter including (i) an elongate shaft having a shaft proximal portion, an opposed shaft distal portion, and a shaft central portion between the shaft proximal portion and the shaft distal portion, and (ii) an ultrasound tip at the shaft distal portion, the ultrasound tip being configured to emit ultrasound signals and receive reflected ultrasound signals; and
a medical sheath including (i) an elongate member having an elongate member proximal portion defining an elongate member proximal end, an opposed elongate member distal portion defining an elongate member distal end, and an elongate member central portion between the elongate member proximal portion and the elongate member distal portion, wherein the elongate member central portion defines a longitudinal axis of the elongate member, and the elongate member distal portion includes a curved section that spaces the elongate member distal end away from the longitudinal axis; (ii) a lumen extending through the elongate member from the elongate member proximal portion to the elongate member distal portion; and (iii) a catch for engaging the shaft of the ultrasound catheter;
wherein the entirety of the shaft is coupled to an outside of the elongate member and extends parallel to the longitudinal axis of the elongate member, such that the ultrasound tip is spaced longitudinally from the elongate member distal end.

12. The medical device assembly of claim 11, wherein the catch comprises a longitudinally extending groove on an exterior surface of the elongate member, and the shaft central portion is received in the groove.

13. The medical device assembly of claim 11, wherein the catch comprises a clip on an exterior surface of the elongate member, and the shaft central portion is received in the clip.

14. The medical device assembly of claim 11, wherein the elongate member is steerable to impart the curved section to the elongate member distal portion.

* * * * *